Figure 1:
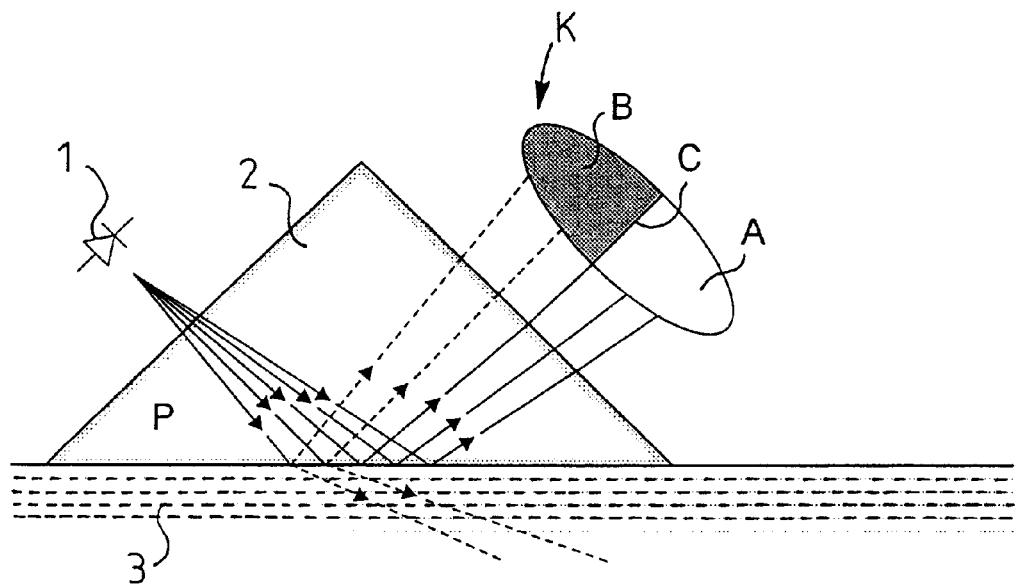

United States Patent [19]

Salo

[11] Patent Number: 6,067,151
[45] Date of Patent: May 23, 2000

[54] REFRACTOMETER

[75] Inventor: Harri Salo, Helsinki, Finland

[73] Assignee: Janesko Oy, Vantaa, Finland

[21] Appl. No.: 09/206,371

[22] Filed: Dec. 7, 1998

[30] Foreign Application Priority Data

Jan. 30, 1998 [FI] Finland ................................. 980221

[51] Int. Cl.⁷ .................................................. G01N 21/41
[52] U.S. Cl. ........................... 356/136; 356/135; 356/128
[58] Field of Search .................................... 356/128, 135, 356/136, 157

[56] References Cited

U.S. PATENT DOCUMENTS 4,749,274  6/1988  Aoki et al. .
5,110,205  5/1992  Suzuki et al. ........................... 356/135
5,477,318  12/1995  Ohsaki et al. .......................... 356/136

FOREIGN PATENT DOCUMENTS 0 281 337 A3  9/1988  European Pat. Off. .
38 31 346 A1  4/1990  Germany .

*Primary Examiner*—Robert H. Kim
*Assistant Examiner*—Zandra V. Smith
*Attorney, Agent, or Firm*—Burns, Doane, Swecker & Mathis, L.L.P.

[57] ABSTRACT

A refractometer, comprising a light source arranged in a frame structure, an optical window to be positioned in a process solution, means for directing a beam of rays from the light source to an interface between the optical window and the process solution, part of the beam of rays being absorbed partly into the solution and part of it being reflected back from the solution entirely and creating an image, in which the location of a borderline between a light area and a dark area depends on the refractive index of the process solution, and an image detector, by means of which the image created in said manner is observed. To eliminate changing angles of the optical window, the light source, the optical window, the means for directing the beam of rays and the image detector are arranged in a rigid analyser module, which is positioned floatingly inside the frame structure to support on a substantially inelastic sealing arranged between the frame structure and the optical window by pressing the analyser module by spring means against the sealing.

5 Claims, 2 Drawing Sheets

REFRACTOMETER

The invention relates to a refractometer, comprising a light source arranged in a frame structure, an optical window to be positioned in a process solution, means for directing a beam of rays from the light source to an interface between the optical window and the process solution, part of the beam of rays being absorbed partly into the solution and part of it being reflected back from the solution entirely and creating an image, in which the location of a borderline between a light area and a dark area depends on the refractive index of the process solution, and an image detector, by means of which the image created in said manner is observed.

The operating principle of the refractometer has been known over a hundred years already. At present, refractometers are used rather much in a plurality of different fields. As examples of the range of use of refractometers can be mentioned food industry, wood-processing industry, chemical industry and researches of different kind, in general.

The operating principle of the refractometer can be described generally as follows. The refractometer measures the refractive index of a process solution by means of the total reflection created at the interface between an optical window and the solution. A beam of rays from a light source is directed to the interface between the optical window and the process solution. Part of the beam of rays is reflected from the solution entirely, part of it is absorbed partly into the solution. This causes an image, in which the location of a borderline between a light area and a dark area depends on the critical angle of the total reflection and thus on the refractive index of the process solution.

An essential feature of refractometer measurement consists in analyzing an image created by light reflection. The purpose of such an image analysis is to find the critical angle of the total reflection, i.e. the borderline at which the light area of the image created in this way turns into a dark area.

As appears from the above facts, the operation of a refractometer is based on a very accurate angle measurement, because the critical angle of the total reflection is determined according to the refractive indexes of two materials. A problem with known refractometers often consists in changing angles between the optical window and the frame structure of the device, because the optical window is often fastened to the frame structure by means of an elastic sealing material. If the optical window is fastened rigidly to the frame structure, the sealing material must be very elastic, and accordingly, certain slightly elastic materials, such as teflon, cannot be used. In several known refractometers, the optics and a light detector are fastened rigidly to the frame, and therefore, another problem is caused by an error in angle measurement due to a distortion of the frame structure.

The object of the invention is to provide a refractometer, by which the drawbacks of the prior art technique can be eliminated. This has been achieved by means of a refractometer according to the invention, which is characterized in that the light source, the optical window, the means for directing the beam of rays and the image detector are arranged in a rigid analyser module, which is positioned floatingly inside the frame structure to support on a substantially inelastic sealing arranged between the frame structure and the optical window by pressing the analyser module by spring means against the sealing.

An advantage of the solution according to the invention is that, thanks to the floating rigid analyser module, a flexible fastening of the optical window is possible also by means of a slightly elastic sealing without the accuracy of the angle measurement suffering. In addition, the structure of the refractometer of the invention is simple, which makes the introduction of the invention advantageous. The refractometer of the invention is also very flexible in use, for it may be mounted in very many ways in the process tube system, for instance.

Figure 2:
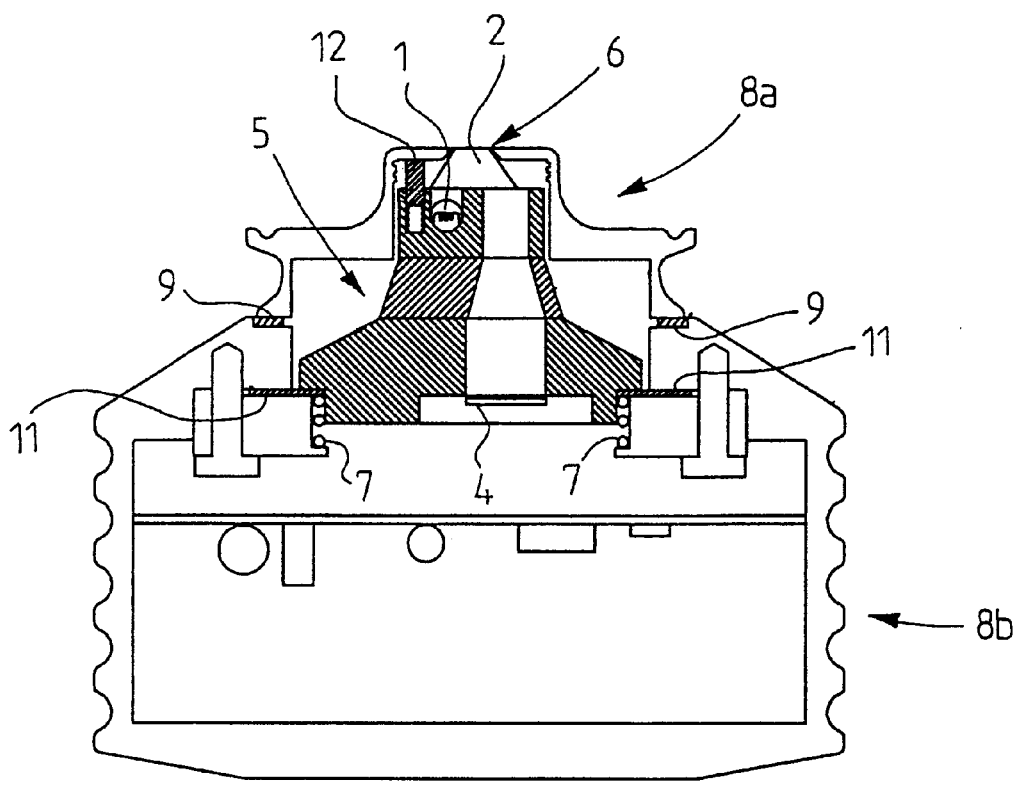
Figure 3:
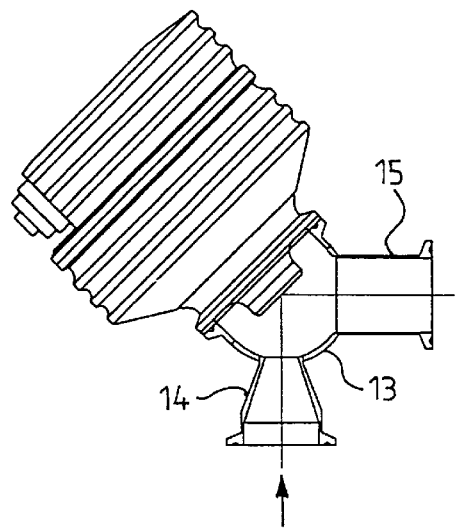
Figure 4:
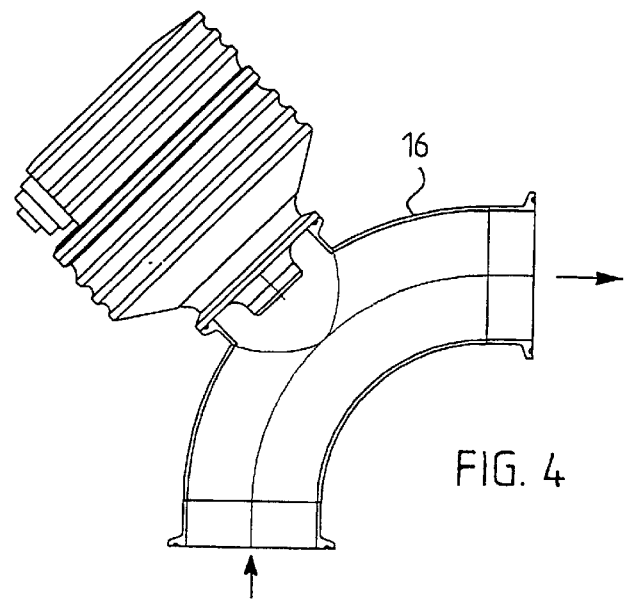
Figure 5:
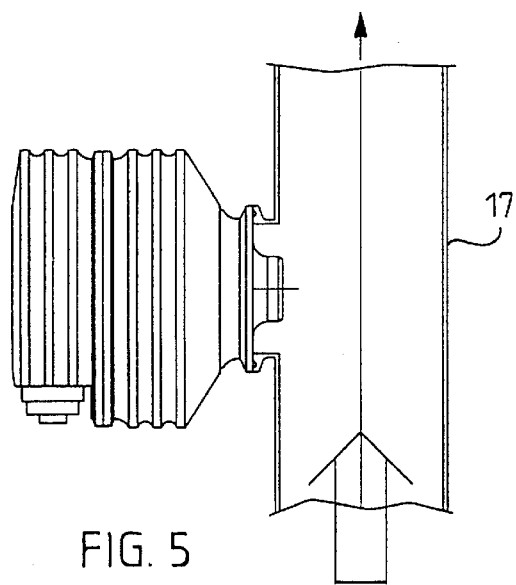

The invention will be described below in greater detail by means of the examples shown in the attached drawing, in which FIG. 1 shows a general diagrammatic plan of the operating principle of a refractometer, FIG. 2 shows a section view of the structure of an embodiment of a refractometer of the invention, in principle, and FIGS. 3 to 5 show examples of various possibilities of mounting the refractometer of the invention.

FIG. 1 shows a general diagrammatic plan of the operating principle of a refractometer. Reference numeral 1 indicates a light source and reference numeral 2 an optical window, which may be a prism, for instance. Reference numeral 3 designates a process solution.

As stated earlier, the refractometer measures the refractive index of the process solution by means of the total reflection created at the interface between the optical window 2 and the process solution 3. The operating principle of the refractometer belongs to the prior art technique fully known to one skilled in the art, and therefore, these facts are not explained here in more detail. In this connection, only the essential basic principle is described.

A beam of rays coming from the light source 1 is directed to the interface between the optical window 2 and the process solution 3. The beam of rays is presented in FIG. 1 by means of arrows, in principle. Part of the beam of rays is reflected back from the process solution 3 entirely, part of it is absorbed partly into the solution. This creates an image K, in which the location of a borderline C of a light area A and a dark area B depends on the critical angle of the total reflection and thus on the refractive index of the process solution.

Accordingly, the operation of the refractometer is based on a very accurate angle measurement, because the critical angle of the total reflection is determined in accordance with the refractive indexes of two materials. As stated above already, a problem with previously known refractometers is often caused by changing angles between the optical window and the frame of the device, because, according to several solutions, the optical window is fastened to the frame by means of an elastic sealing material. Using elastic material as a seal is due to the fact that, if the optical window is fastened rigidly to the frame, the sealing material has to be very elastic, and accordingly, slightly elastic materials cannot be used. In many known refractometers, the optics and a light detector are fastened rigidly to the frame, and therefore, another problem is caused by an error in angle measurement due to a distortion of the frame.

It has been possible to eliminate the above-mentioned drawbacks of the prior art technique by means of the refractometer of the invention. The essential feature of the refractometer of the invention is that the light source 1, the optical window 2, the means for directing the beam of rays and the image detector 4 are arranged in a rigid analyser module 5. The optical window may be a prism, for instance. The image detector may be a row CCD element, for instance. The analyser module 5 is positioned floatingly inside the frame structure to support on a substantially inelastic sealing 6 arranged between the frame structure and the optical window 2. For example, the sealing may be a conical sealing or it may form a spherical surface, and so on. Because the analyser module 5 floats supported on the sealing 6 with respect to the frame structure and other mechanics of the device, outer forces, such as forces caused by the flow of the process solution, mechanical stresses in the tube system, heat expansion and pressure, do not affect the accuracy of the measurement. Thanks to the floating analyser module 5, slightly elastic materials, such as teflon, can also be used for the sealing 6 of the prism.

The analyser module 5 is pressed by means of spring means 7 against the sealing 6, the pressing force being constant at all temperatures. Consequently, the spring means 7 together with the floating analyser module 5 compensate for the slight elasticity of certain sealing materials. The spring means are mounted in such a way that no process heat flows through them into the analyser module 5.

The floating analyser module 5 is in contact with the process solution 3 and a point 8a of the frame structure, i.e. that part of the frame structure which is in contact with the process, through the optical window 2 only. The contact face with the process and the point of the frame structure is minimized in order to prevent heat conduction. There is a sealing 6 between the optical window 2 and the point. The contact face shall allow slightly changing angles between the axis of the analyser module and the axis of the point. As stated above, the contact face of the sealing may be conical or spherical, for instance. Thanks to the floating analyser module 5, the device is easy to manufacture and maintain as well. The analyser can be tested even before it is actually connected to the rest of the mechanics.

In process measuring devices, heat transfer from the process to the electronics and to other heat sensitive components has to be minimized, and on the other hand, cooling these parts has to be maximized. An accurate measurement of concentration also requires an accurate and rapid temperature measurement of the process solution. In the refractometer of the invention, heat is transferred both through the frame structure and the analyser module to the electronics. Heat conduction through the frame structure has been prevented by making the wall thickness of the point 8a thinner and by positioning a heat insulation 9 between the point 8a and the rest of the frame structure, e.g. a cover part 8b. A suitable material for the heat insulation 9 is teflon, for instance.

Heat may be conducted into the analyser module 5 through the optical window 2 and the sealing 6 only. Radiation heat enters through the walls of the point 8a. Heat transfer through the analyser module 5 to the electronics is prevented by means of a separate rigid insulation part 10, forming part of the analyser module. The insulation part 10 shall be rigid, and therefore, certain ceramics, for instance, are suitable insulations.

The heat penetrating the insulation part 10 of the analyser module 5 is conducted efficiently to the frame structure by a flexible heat conductor 11, which is plate-shaped, for instance. The heat conductor 11 to be positioned between the analyser module 5 and the frame structure is made of a material conducting heat well, such as copper or aluminium, and its structure allows a movement in the axial direction of the analyser module 5. The heat is conducted from the frame structure to the environment of the device by means of the big outer surface area of the frame structure. The outer surface area of the frame structure can be increased for instance by a suitable ribbing of the cover part 8b, as is shown in the figures.

In connection with the refractometer of the invention, the temperature measurement of the process solution can be carried out in a particularly advantageous manner. The temperature of the process solution is measured by means of an electric temperature sensor 12. The heat contact of the temperature sensor 12 is maximized in the direction of the point 8a and minimized in the direction of the rest of the mechanics. The temperature sensor 12 is insulated against the analyser module 5 by means of a suitable insulating material, such as teflon. The rapidity of temperature measurement is influenced, besides by the mass of the sensor, also by the mass of the point 8a. To provide a sufficiently rapid temperature measurement, the mass of the point can be divided into two different parts. The temperature sensor is in direct contact with the lighter part. Heat conduction between the small and the big part can be reduced by making the wall thinner without weakening the mechanical pressing rigidity of the point.

The refractometer of the invention is normally mounted in the main flow, i.e. it is a so-called in-line measuring device. Because of the optical measuring method, the optical window shall keep clean. The mounting site of the device is important for keeping the window clean. In tube systems having a relatively high flow rate, the bends of the tube system keep clean. Accordingly, it is preferable to choose just a tube bend as the mounting site of the device of the invention. If the tube has a small size, a special flow vessel 13 can be used, which is mounted in the place of a standard tube bend. FIG. 3 shows such a flow vessel. The flow vessel comprises a hemisphere, the midpoint of which is the optical window of the measuring device. Inlets and outlets 14, 15 of the flow vessel are directed to the midpoint of the hemisphere and they form a 90 degree angle with each other. If the cleaning effect caused by the flow shall be increased, the inlet 14 can be slightly reduced, as disclosed in the example of FIG. 3. The flow vessel empties itself when it is mounted into the position according to FIG. 3. As far as flow technique is concerned, the inlet and outlet can be easily connected to the hemisphere, because the contact face of a sphere and a cylinder is a circle.

The refractometer of the invention can be mounted in rather big tubes, at a tube bend 16, in the manner shown in FIG. 4. The refractometer of the invention can naturally also be mounted directly in a tube 17, as is shown in FIG. 5. The flow directions of the process solution are marked with arrows in the FIGS. 3 to 5.

The above embodiments are not intended to restrict the invention in any way, but the invention can be modified within the scope of the claims fully freely. Accordingly, it is clear that the refractometer of the invention does not necessarily need to be just as shown in the figures, but solutions of other kinds are also possible.

I claim:

1. A refractometer, comprising a light source arranged in a frame structure, an optical window to be positioned in a process solution, means for directing a beam of rays from the light source to an interface between the optical window and the process solution, part of the beam of rays being absorbed partly into the solution and part of it being reflected back from the solution entirely and creating an image, in which the location of a borderline between a light area and a dark area depends on the refractive index of the process solution, and an image detector, by means of which the image created in said manner is observed, wherein the light source, the optical window, the means for directing the beam of rays and the image detector are arranged in a rigid analyser module, which is positioned floatingly inside the frame structure to support on a substantially inelastic sealing arranged between the frame structure and the optical window by pressing the analyser module by spring means against the sealing.

2. A refractometer according to claim 1, wherein the frame structure comprises a point part and a cover part and a heat insulation is arranged between the point part and the cover part.

3. A refractometer according to claim 1, wherein a rigid insulation part preventing heat conduction is arranged in the analyser module.

4. A refractometer according to claim 3, wherein a heat conductor is arranged between the analyser module and the cover part.

5. A refractometer according to claim 4, wherein the heat conductor is a part which is flexible in the axial direction of the analyser module.

* * * * *